US009854995B2

(12) United States Patent
Demirdjian et al.

(10) Patent No.: US 9,854,995 B2
(45) Date of Patent: Jan. 2, 2018

(54) NON-INVASIVE, NON CONTACT SYSTEM, ELECTRONIC CONTROL UNIT, AND ASSOCIATED METHODOLOGY FOR MINIMIZING MUSCLE STRESS AND IMPROVING CIRCULATION

(75) Inventors: David Demirdjian, Somerville, MA (US); Chenna K. Varri, Quincy, MA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 1248 days.

(21) Appl. No.: 12/479,306

(22) Filed: Jun. 5, 2009

(65) Prior Publication Data

US 2010/0312142 A1 Dec. 9, 2010

(51) Int. Cl.
| | | |
|---|---|---|
| *A61B 5/103* | (2006.01) | |
| *A61B 5/00* | (2006.01) | |
| *B60N 2/00* | (2006.01) | |
| *B60N 2/02* | (2006.01) | |
| *A61B 5/01* | (2006.01) | |

(52) U.S. Cl.
CPC ............ *A61B 5/103* (2013.01); *A61B 5/4519* (2013.01); *B60N 2/002* (2013.01); *B60N 2/0244* (2013.01); *A61B 5/015* (2013.01); *B60N 2002/0268* (2013.01)

(58) Field of Classification Search
CPC ....... A61B 5/015; A61B 5/103; A61B 5/4519; A61F 7/007; B60N 2/002; B60N 2/0244; B60N 2/0248; B60N 2/0252; B60N 2/5685; B60N 2002/0268; B60H 1/2218; B60H 1/00742; B60H 2001/2293

USPC ......... 600/587, 549, 595; 340/576; 219/202, 219/217
See application file for complete search history.

(56) References Cited

U.S. PATENT DOCUMENTS

| | | | |
|---|---|---|---|
| 4,625,329 A * | 11/1986 | Ishikawa et al. ............. 382/104 |
| 5,187,943 A | 2/1993 | Taniguchi et al. | |
| 5,237,870 A * | 8/1993 | Fry et al. ........................ 73/588 |
| 5,263,765 A * | 11/1993 | Nagashima et al. ........ 297/284.6 |
| 5,398,185 A * | 3/1995 | Omura ............. B60R 21/01538 180/268 |
| 5,523,664 A * | 6/1996 | Ogasawara .................... 318/590 |
| 5,748,473 A * | 5/1998 | Breed et al. .................... 701/45 |
| 5,829,782 A | 11/1998 | Breed et al. | |
| 5,930,152 A * | 7/1999 | Dumont ............... B60N 2/0224 128/845 |
| 6,512,364 B1 * | 1/2003 | Okada ........................... 73/1.08 |
| 6,550,686 B2 | 4/2003 | Kawai et al. | |
| 6,726,276 B1 * | 4/2004 | Tholkes et al. ............... 297/172 |
| 6,922,622 B2 | 7/2005 | Dulin et al. | |

(Continued)

FOREIGN PATENT DOCUMENTS

WO    WO 2007123127 A1 * 11/2007

*Primary Examiner* — Rene Towa
(74) *Attorney, Agent, or Firm* — Oblon, McClelland, Maier & Neustadt, L.L.P.

(57) ABSTRACT

A method, system, and process are described to decrease muscle fatigue and improve circulation of an individual resting on a support device, such as an adjustable chair or bed. The body pose and heat distribution of the individual are determined and used to estimate muscle fatigue and circulation. The estimated muscle fatigue and circulation are then used to determine settings for the support device or the temperature of the environment.

17 Claims, 4 Drawing Sheets

(56) References Cited

U.S. PATENT DOCUMENTS

| | | | |
|---|---|---|---|
| 7,027,621 B1* | 4/2006 | Prokoski | 382/118 |
| 7,077,812 B2* | 7/2006 | Naghavi | 600/587 |
| 7,198,605 B2* | 4/2007 | Donofrio et al. | 600/559 |
| 7,319,386 B2* | 1/2008 | Collins et al. | 340/539.12 |
| 7,430,467 B2 | 9/2008 | Borke | |
| 7,821,409 B2* | 10/2010 | Ishida | 340/576 |
| 2001/0005074 A1* | 6/2001 | Sakai et al. | 280/728.1 |
| 2002/0029410 A1* | 3/2002 | Szymocha et al. | 2/458 |
| 2002/0170193 A1* | 11/2002 | Townsend et al. | 33/512 |
| 2003/0038722 A1 | 2/2003 | Khairallah et al. | |
| 2004/0057645 A1* | 3/2004 | Willner | 385/12 |
| 2004/0201481 A1* | 10/2004 | Yoshinori et al. | 340/575 |
| 2005/0027416 A1* | 2/2005 | Basir et al. | 701/36 |
| 2005/0278094 A1* | 12/2005 | Swinbanks et al. | 701/37 |
| 2007/0045266 A1* | 3/2007 | Sandberg et al. | 219/207 |
| 2007/0045267 A1* | 3/2007 | Vinegar et al. | 219/207 |
| 2007/0102969 A1* | 5/2007 | Phipps | 297/180.12 |
| 2008/0119994 A1 | 5/2008 | Kameyama | |
| 2008/0122799 A1* | 5/2008 | Pryor | G06F 3/0312 345/173 |
| 2008/0291032 A1* | 11/2008 | Prokhorov et al. | 340/576 |
| 2008/0312796 A1 | 12/2008 | Matsuura et al. | |
| 2010/0130808 A1* | 5/2010 | Hattori | 600/9 |

* cited by examiner

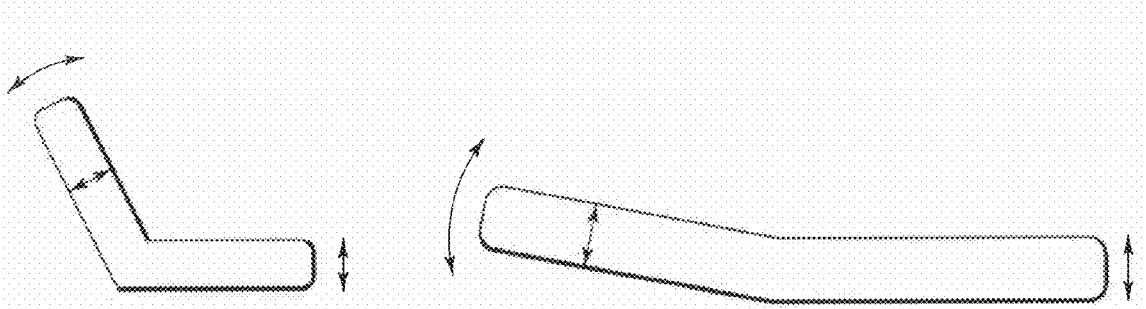
*Fig. 1A*     *Fig. 1B*
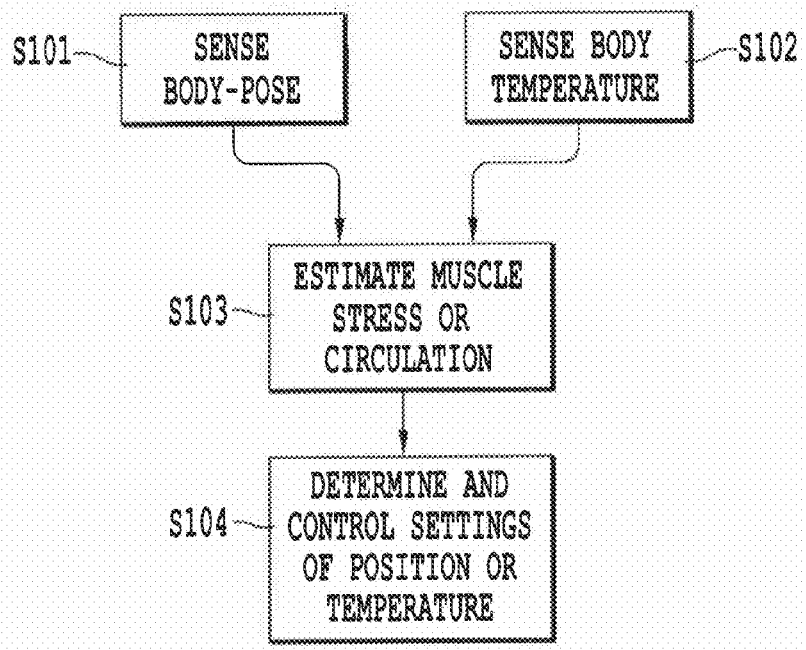
*Fig. 2*

Thermal Imaging Data    3D Body Pose Data

Adjust Temperature system

Adjust Seat Alignment, posture and shape.

NON-INVASIVE, NON CONTACT SYSTEM, ELECTRONIC CONTROL UNIT, AND ASSOCIATED METHODOLOGY FOR MINIMIZING MUSCLE STRESS AND IMPROVING CIRCULATION

BACKGROUND OF THE INVENTION

Field of the Invention

The present invention relates generally to a system and method for minimizing muscle stress or improving blood circulation of a person on a support device such as a seat or a bed.

Description of the Related Art

Adjustment means for increasing comfort, such as adjustable car seats and hospital beds, depicted at FIG. 1, for example, as well as seats and beds that adjust to pre-programmed positions stored in memory, are known. Automatic adjustment of temperature to a preset value, in a room or a vehicle, for example, is also known. As depicted at FIG. 1, lumbar support, height, and incline of the back are among the adjustments that are typically found in adjustable seats and beds.

Safety systems that detect presence, of occupants in a vehicle, for example, and thermal imaging systems detecting the external environment of a car are also known. A vehicle occupant detection system may be used to activate or deactivate airbags or start the engine and cooling system to decrease the temperature if a child is locked in a car, for example. Thermal imaging systems are described which detect people or animals in the path of a vehicle on a dark road.

While these existing systems can improve comfort and increase safety, none takes into account muscle fatigue or circulation issues of an individual.

SUMMARY OF THE INVENTION

The present invention is directed to improving comfort and safety of a person by minimizing muscle stress or improving circulation based on sensed data of the person's body pose and body heat distribution.

A method of minimizing muscle stress or increasing circulation of a person resting on a support device in an environment includes sensing body pose of the person, sensing body heat distribution of the person, estimating muscle stress or circulation based on the sensed body pose and the sensed body heat distribution, and determining a setting of at least one of the support device or temperature of the environment based on the estimated muscle stress or circulation.

A system configured to minimize muscle stress or improve circulation of a person on a support device in an environment includes a body pose sensor configured to sense body pose of the person, a body temperature sensor configured to sense body heat distribution of the person, an estimator configured to estimate muscle stress or circulation of the person based on the sensed body pose and the sensed body heat distribution, and a controller configured to adjust a setting of the support device or temperature of the environment based on the estimated muscle stress or circulation.

A process, implemented in a feedback loop, of minimizing muscle stress or improving circulation of a person on a support device in an environment includes sensing body pose and body heat distribution of the person, estimating muscle stress or circulation based on the sensed body pose and the sensed body heat distribution, determining setting of the support device or temperature of the environment to reduce muscle stress or to improve circulation, and controlling the setting according to the determined setting.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 depicts example support devices with exemplary adjustments.

FIG. 2 illustrates a method of determining a setting for a support device or temperature of an environment based on sensed data used to estimate muscle fatigue and body heat distribution for a person on the support device.

DETAILED DESCRIPTION OF THE PREFERRED EMBODIMENTS

FIG. 2 depicts the steps involved in determining a setting for a support device or temperature of an environment based on sensed data of body pose and body temperature for a person on the support device. The step of sensing body pose is depicted at S101, and the step of sensing body temperature is depicted at S102.

Body pose, sensed at step S101, can be used to identify different body parts. The corresponding sensing of body temperature can be used to determine body heat distribution over the identified body parts.

Estimating muscle stress or circulation is depicted at S103. Muscle stress can lead to muscle fatigue and long-term injuries, and reduced circulation can lead to headache, leg and chest pain, and dizziness, for example. Both muscle stress and circulation, as well as other physiological conditions, could be estimated at step S103.

Settings are determined and controlled, as depicted at step S104, for the support device and/or temperature of the environment based on the result of the estimating step at S103.

Figure 3:
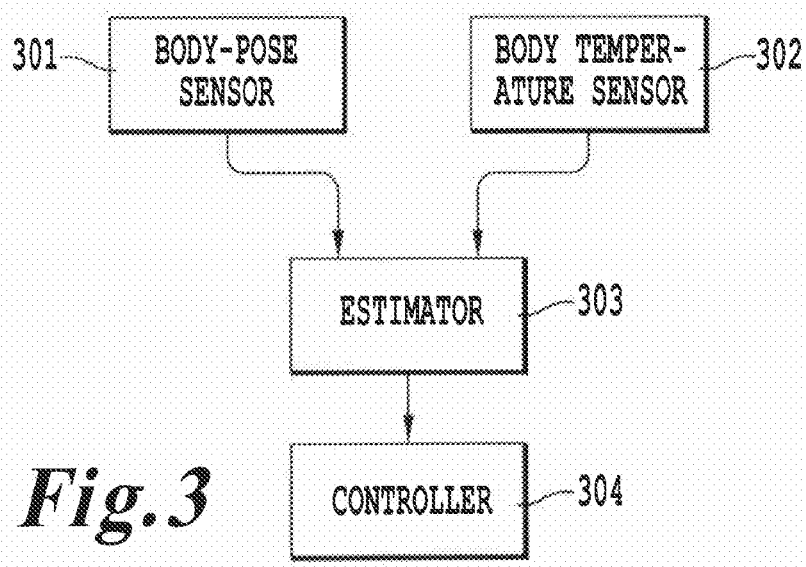
FIG. 3 depicts a system that determines settings of a support device or temperature of an environment based on sensor data of body pose and body heat distribution of a person on the support device.

FIG. 3 depicts a system that determines settings of a support device or temperature of an environment based on sensor data of body pose and body temperature of a person on the support device.

The body-pose sensor 301 can be comprised of one or more of a 2D camera, a 3D camera, and a 3D sensor, along with an image processor, for example. Devices and systems for detecting and identifying body parts are known in the pertinent art.

The body temperature sensor 302 can be a heat sensing device, an infrared imaging device, a heat-detecting imaging device, or the like. Devices and systems for detecting heat distribution over a given area are known in the pertinent art.

The estimator 303 can be part of a larger processing system and may implement a decision tree matching body heat concentration patterns to known or generated rules regarding muscle stress and/or circulation. The estimator 303 could also be implemented as a stand-alone processor.

The controller 304 can be comprised of one or more devices and can be implemented as part of a larger system, either the same as or different from a system including the estimator 303. The controller 304 determines settings of the support device supporting the person sensed by the body-pose sensor 301 and body heat distribution determined with the body temperature sensor 302 and/or of the temperature of the environment of the person, based on the estimator 303 output. The controller 304 may implement a decision tree or other machine learning system to determine the settings needed to reduce the estimated muscle stress or increase the estimated circulation.

FIG. 4 depicts a non-limiting example of a system in a vehicle. As depicted at FIGS. 4a and 4b, body-pose sensors and body temperature sensors may be positioned at various locations in the vehicle depending on which vehicle occupant(s) is the target of the system. FIG. 4c illustrates the type of images that may be captured by the sensors. FIG. 4d depicts the type of adjustments that may be made to the vehicle seat based on an estimation of muscle stress and/or circulation resulting from the sensor data. Additionally, the temperature in the vehicle may be controlled based on the estimation resulting from the sensor data.

One of ordinary skill in the pertinent art will readily understand that the herein-described method and system has numerous uses beyond the above-discussed example. Another non-limiting exemplary usage environment is an airplane. The implementation of the herein-described method and system on an airplane can be used, for example, to prevent deep vein thrombosis related to long flights.

Still further uses include monitoring patients and adjusting hospital beds to decrease muscle fatigue and improve circulation. Long-haul truck drivers with exemplary systems installed in their truck cabs to control settings of the driver's seat, a bed in the back of the truck cab, and/or the cab temperature can improve alertness by decreasing muscle fatigue and increasing circulation while sitting in the driving seat and/or while sleeping in the back portion of the cab.

Figure 5:
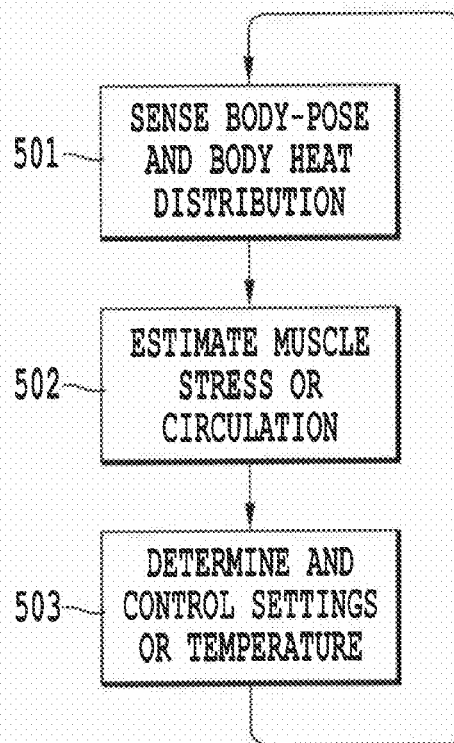
FIG. 5 depicts an on-going process of sensing body pose and body heat distribution, estimating muscle stress and/or circulation and controlling settings or temperature.
Figure 4A:
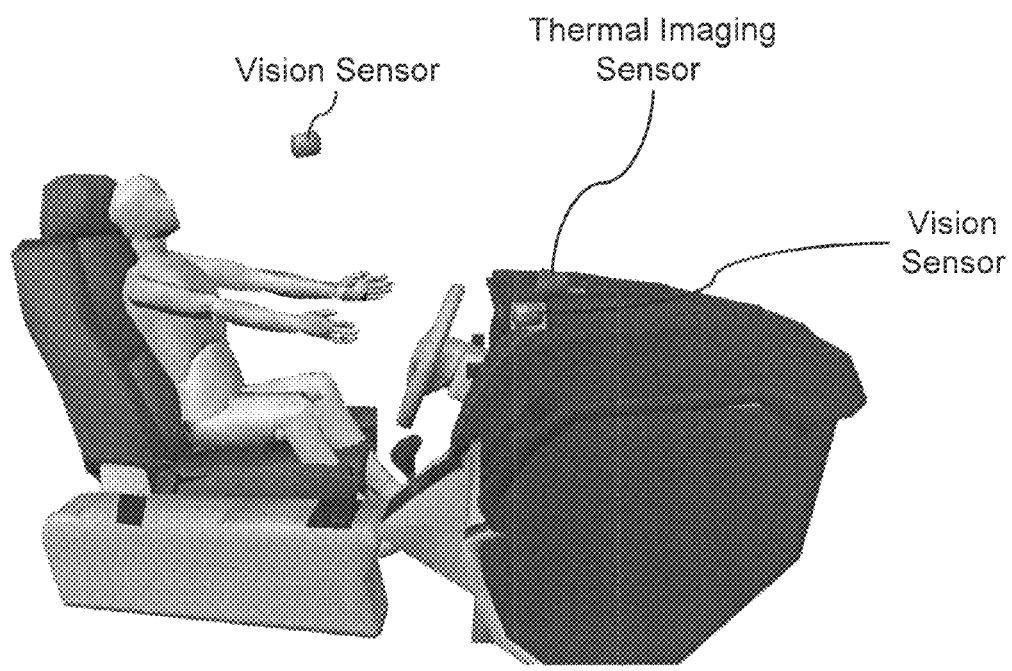
FIG. 4 depicts non-limiting exemplary sensors and environment.
Figure 4B:
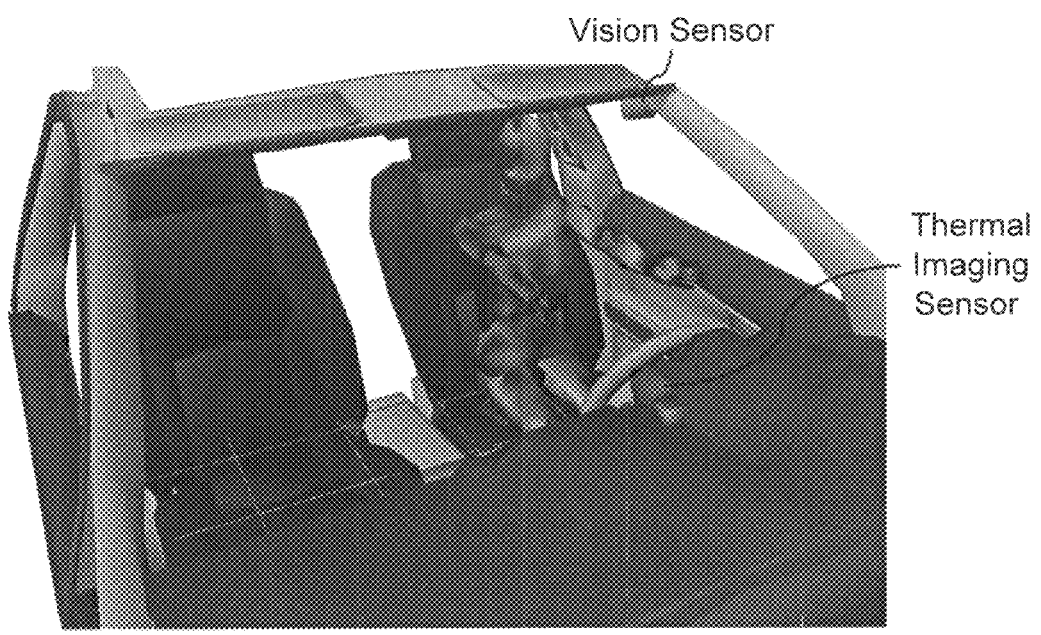
Figure 4C:
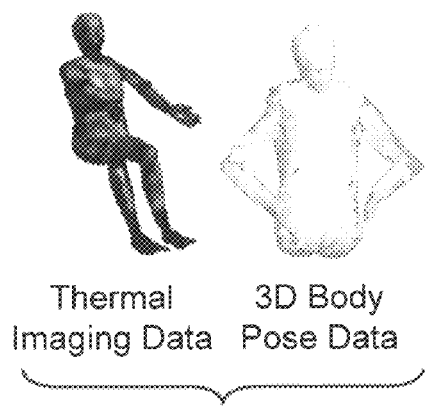
Figure 4D:
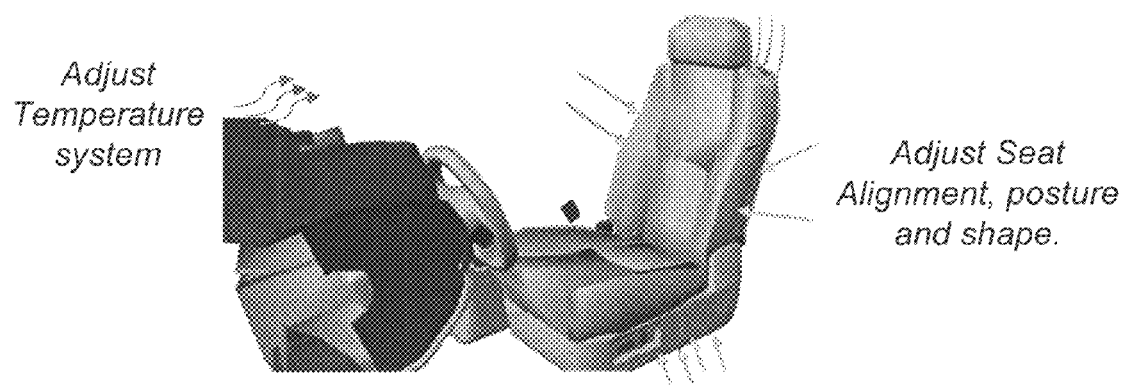

In a given usage environment, the method and system can be implemented on an on-going basis as depicted at FIG. 5. Body pose and body heat distribution is sensed at step 501, muscle stress or circulation is estimated, based on the sensed data, at step 502, and settings or temperature are controlled at step 503. The frequency of the sensing and controlling steps can be adjusted as needed for a given usage condition and environment.

With regard to processors discussed above, to implement the estimator 303, controller 304, or other components of the system described herein, exemplary processors/microprocessor and storage medium(s) are listed herein and should be understood by one of ordinary skill in the pertinent art as non-limiting. Microprocessors used to perform the methods of the present invention could utilize a computer readable storage medium, such as a memory (e.g. ROM, EPROM, EEPROM, flash memory, static memory, DRAM, SDRAM, and their equivalents), but, in an alternate embodiment, could further include or exclusively include a logic device for augmenting or fully implementing the present invention. Such a logic device includes, but is not limited to, an application-specific integrated circuit (ASIC), a field programmable gate array (FPGA), a generic-array of logic (GAL), an Electronic Control Unit (ECU), and their equivalents. The microprocessors can be separate devices or a single processing mechanism.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of minimizing muscle stress or increasing blood circulation of a person resting on a support device in an environment, the method comprising:
    sensing, by a body pose sensor, a body pose of the person using a first image sensor located above head level of the person and a second image sensor located below the head level of the person in order to capture a three-dimensional image of at least a torso of the person, the three-dimensional image being used to determine the body pose of the person;
    sensing, by a body temperature sensor, a body heat distribution of the person over a plurality of different body parts of the person;
    determining, by circuitry, at least one of a muscle stress estimate and a blood circulation estimate of the person based only on the sensed body pose and the sensed body heat distribution; and
    controlling a positional adjustment of the support device according to the at least one of the muscle stress estimate and the blood circulation estimate.

2. The method according to claim 1, wherein the support device is an adjustable seat.

3. The method according to claim 1, wherein the support device is a hospital bed.

4. An electronic control unit (ECU) implementing the method according to claim 1, wherein the support device is a vehicle seat.

5. The method according to claim 1, further comprising:
    determining a setting of a temperature of the environment based on the at least one of the muscle stress estimate and the blood circulation estimate.

6. A system configured to minimize muscle stress or improve blood circulation of a person on a support device in an environment, the system comprising:
    a body pose sensor configured to sense a body pose of the person, the body pose sensor including a first image sensor located above head level of the person and a second image sensor located below the head level of the person in order to capture a three-dimensional image of at least a torso of the person, the three-dimensional image being used to determine the body pose of the person;
    a body temperature sensor configured to sense a body heat distribution of the person over a plurality of different body parts of the person;
    circuitry configured to
        determine at least one of a muscle stress estimate and a blood circulation estimate of the person based only on the sensed body pose and the sensed body heat distribution; and
        control a positional adjustment of the support device according to the at least one of the muscle stress estimate and the blood circulation estimate.

7. The system according to claim 6, wherein the body temperature sensor is a heat-detecting imaging device.

8. The system according to claim 6, wherein the support device is a vehicle seat.

9. The system according to claim 6, wherein the support device is a hospital bed.

10. The system according to claim 6, wherein the circuitry includes a controller that is part of an electronic control unit (ECU).

11. The system according to claim 6, wherein the circuitry is further configured to determine a setting of a temperature of the environment based on the at least one of the muscle stress estimate and the blood circulation estimate.

12. The system according to claim 6, wherein the circuitry is configured to determine the at least one of the muscle stress estimate and the blood circulation estimate by matching body heat concentration patterns to predetermined rules regarding at least one of muscle stress and blood circulation.

13. The system according to claim 6, wherein the circuitry is configured to
identify different body parts of the person based on the sensed body pose of the person, and
determine the body heat distribution over the identified body parts.

14. The system according to claim 6, wherein the circuitry is configured to implement
an estimator configured to determine the at least one of the muscle stress estimate and the blood circulation estimate, and output the at least one of the muscle stress estimate and the blood circulation estimate to a controller, and
the controller is configured to determine a setting for the support device based on the at least one of the muscle stress estimate and the blood circulation estimate output by the estimator.

15. The system according to claim 6, wherein the circuitry is configured to determine both the muscle stress estimate and the blood circulation based only on the sensed body pose and the sensed body heat distribution.

16. A non-transitory computer-readable medium storing instructions which when executed by a computer causes the computer to perform a process of minimizing muscle stress or improving blood circulation of a person on a support device in an environment, the process comprising:
sensing a body pose of the person using a first image sensor located above head level of the person and a second image sensor located below the head level of the person in order to capture a three-dimensional image of at least a torso of the person, the three-dimensional image being used to determine the body pose of the person;
sensing a body heat distribution of the person over a plurality of different body parts of the person;
determining at least one of a muscle stress estimate and a blood circulation estimate of the person based only on the sensed body pose and the sensed body heat distribution; and
controlling a positional adjustment of the support device according to the at least one of the muscle stress estimate and the blood circulation estimate.

17. The non-transitory computer-readable medium according to claim 16, wherein the process further comprises:
determining a setting of a temperature of the environment based on the at least one of the muscle stress estimate and the blood circulation estimate.

* * * * *